US00PP22688P2

(12) United States Plant Patent
Saul

(10) Patent No.: US PP22,688 P2
(45) Date of Patent: Apr. 24, 2012

(54) *ECHINACEA* PLANT NAMED 'JACOB LEWIS'

(50) Latin Name: *Echinacea purpurea×Echinacea paradoxa*
Varietal Denomination: Jacob Lewis

(75) Inventor: Richard Gregg Saul, Cleveland, GA (US)

(73) Assignee: Itsaul Plants LLC, Alpharetta, GA (US)

( * ) Notice: Subject to any disclaimer, the term of this patent is extended or adjusted under 35 U.S.C. 154(b) by 214 days.

(21) Appl. No.: 12/798,024

(22) Filed: Mar. 27, 2010

(51) Int. Cl.
*A01H 5/00* (2006.01)

(52) U.S. Cl. ..... Plt./428

(58) Field of Classification Search ..... Plt./428
See application file for complete search history.

(56) References Cited

U.S. PATENT DOCUMENTS

PP17,659 P2 * 4/2007 Saul ..... Plt./428
PP18,783 P2 * 5/2008 Saul ..... Plt./428

OTHER PUBLICATIONS

Anonymous. *Echinaceas Echinacea* database: 'Jupiter' (Also known as Jacob Lewis—Big Sky Series) date unknown. Accessed Jul. 12, 2011 available at http://cubits.org/echinaceae/db/echinaceasultivars/view/15750.*

* cited by examiner

*Primary Examiner* — Wendy C Haas
(74) *Attorney, Agent, or Firm* — C. A. Whealy

(57) ABSTRACT

A new and distinct cultivar of *Echinacea* plant named 'Jacob Lewis', characterized by its upright to somewhat outwardly spreading and columnar plant habit; vigorous growth habit; freely branching habit; large single fragrant inflorescences with salmon orange-colored ray florets; strong flowering stems that hold the inflorescences upright; and good garden performance.

2 Drawing Sheets

Botanical designation: *Echinacea purpurea×Echinacea paradoxa.*

Cultivar denomination: 'JACOB LEWIS'.

BACKGROUND OF THE INVENTION

The present invention relates to a new and distinct cultivar of *Echinacea* plant, botanically known as *Echinacea purpurea×Echinacea paradoxa* and hereinafter referred to by the name 'Jacob Lewis'.

The new *Echinacea* plant originated from an open-pollination during the summer of 2003 of two unnamed selections of *Echinacea purpurea×Echinacea paradoxa*, not patented. The new *Echinacea* plant was discovered and selected by the Inventor as a single flowering plant from within the progeny of the stated open-pollination grown in a controlled outdoor nursery environment in Dahlonega, Ga. in June, 2004.

Asexual reproduction of the new Echinacea plant by tissue culture in a controlled environment in Alpharetta, Ga. since 2006, has shown that the unique features of this new *Echinacea* plant are stable and reproduced true to type in successive generations.

SUMMARY OF THE INVENTION

Plants of the new *Echinacea* have not been observed under all possible environmental conditions. The phenotype may vary somewhat with variations in environment such as temperature and light intensity, without, however, any variance in genotype.

The following traits have been repeatedly observed and are determined to be the unique characteristics of 'Jacob Lewis'. These characteristics in combination distinguish 'Jacob Lewis' as a new and distinct cultivar of *Echinacea:*

1. Upright to somewhat outwardly spreading and columnar plant habit.
2. Vigorous growth habit.
3. Freely branching habit.
4. Large single fragrant inflorescences with salmon orange-colored ray florets.
5. Strong flowering stems that hold the inflorescences upright.
6. Good garden performance.

Plants of the new *Echinacea* differ from plants of the parent selections primarily in ray floret color.

Plants of the new *Echinacea* can be compared to plants of *Echinacea purpurea* 'Evan Saul', disclosed in U.S. Plant Pat. No. 17,659. In side-by-side comparisons conducted in Dahlonega, Ga., plants of the new *Echinacea* differed from plants of 'Evan Saul' in the following characteristics:

1. Plants of the new *Echinacea* were taller than plants of 'Evan Saul'.
2. Plants of the new *Echinacea* had larger inflorescences than plants of 'Evan Saul'.
3. Plants of the new *Echinacea* and 'Evan Saul' differed in ray floret color as plants of 'Evan Saul' had orange-colored ray florets.

Plants of the new *Echinacea* can be compared to plants of *Echinacea purpurea* 'Katie Saul', disclosed in U.S. Plant Pat. No. 18,783. In side-by-side comparisons conducted in Dahlonega, Ga., plants of the new *Echinacea* differed from plants of 'Katie Saul' in the following characteristics:

1. Plants of the new *Echinacea* were taller than plants of 'Katie Saul'.
2. Plants of the new *Echinacea* had larger inflorescences than plants of 'Katie Saul'.

3. Plants of the new *Echinacea* and 'Katie Saul' differed in ray floret color as plants of 'Katie Saul' had salmon pink-colored ray florets.

BRIEF DESCRIPTION OF THE PHOTOGRAPHS

The accompanying photographs illustrate the overall appearance of the new *Echinacea* plant. The photographs show the colors as true as it is reasonably possible to obtain in colored reproductions of this type. Colors in the photographs may differ slightly from the color values cited in the detailed botanical description which accurately describe the colors of the new *Echinacea* plant.

The photograph on the first sheet comprises a side perspective view of typical flowering plants of 'Jacob Lewis' grown in an outdoor nursery.

The photograph on the second sheet is a close-up view of typical inflorescences of 'Jacob Lewis'.

DETAILED BOTANICAL DESCRIPTION

The aforementioned photographs and following observations and measurements describe plants grown in Alpharetta, Ga. during the summer in an outdoor nursery and under conditions and practices which approximate those generally used in commercial *Echinacea* production. During the production of the plants, day temperatures averaged 27° C. and night temperatures averaged 18° C. Measurements and numerical values represent averages for typical flowering plants. Plants were one year old when the photographs and description were taken. In the following description, color references are made to The Royal Horticultural Society Colour Chart, 2007 Edition, except where general terms of ordinary dictionary significance are used.

Botanical classification: *Echinacea purpurea*×*Echinacea paradoxa* 'Jacob Lewis'.

Parentage:

*Female parent*.—Unnamed selection of *Echinacea purpurea*×*Echinacea paradoxa*, not patented.

*Male parent*.—Unnamed selection of *Echinacea purpurea*×*Echinacea paradoxa*, not patented.

Propagation:

*Type*.—By tissue culture.

*Time to initiate roots*.—About 15 days at 20° C. to 23° C.

*Time to produce a rooted young plant, summer*.—About eight weeks at 26° C.

*Time to produce a rooted young plant, winter*.—About ten weeks at 21° C.

*Root description*.—Fleshy, medium in thickness; white in color.

*Rooting habit*.—Freely branching; moderately dense.

Plant description:

*Plant form/growth habit*.—Upright to somewhat outwardly spreading and columnar plant habit; freely basal branching with numerous basal branches; terminal and axillary inflorescences potentially developing at every node and are held upright on strong peduncles; vigorous growth habit.

*Plant height*.—About 51 cm.

*Plant diameter or spread*.—About 41 cm.

*Basal branches*.—Length: About 44 cm. Diameter, towards the base: About 8 mm. Internode length: About 3.3 cm. Aspect: Upright to slightly outwardly leaning. Strength: Strong. Texture: Glabrous; longitudinally ridged. Color: Close to 146A to 146B.

Foliage description:

*Arrangement*.—Alternate, simple.

*Length*.—About 11.5 cm.

*Width*.—About 3.75 cm.

*Shape*.—Narrowly elliptical to lanceolate.

*Apex*.—Sharply acute, elongated.

*Base*.—Attenuate.

*Margin*.—Shallowly serrated.

*Texture, upper and lower surfaces*.—Rough, sparsely pubescent.

*Venation pattern*.—Palmate, reticulate.

*Color*.—Developing and fully expanded leaves, upper surface: Close to 147A; venation, close to 146A. Developing and fully expanded leaves, lower surface: Close to 147B; lateral veins, close to 147B; midvein, close to 147C.

*Petiole*.—Length: About 33 cm. Diameter: About 7 mm. Texture, upper and lower surfaces: Sparsely pubescent. Color, upper surface: Center, close to 147C; towards the margins, close to 147A. Color, lower surface: Center, close to 147C; towards the margins, darker than 147B.

Inflorescence description:

*Appearance*.—Rotate single inflorescence form with ray and disc florets; inflorescences terminal or axillary; inflorescences potentially developing at every node with one to about three open inflorescences per lateral branch at one time; inflorescences held upright on strong peduncles.

*Fragrance*.—Moderate; sweet, pleasant.

*Time to flower*.—Plants flower continuously from the spring throughout the summer in Georgia.

*Inflorescence longevity*.—Depending on temperatures, inflorescences maintain good substance for about two to four weeks on the plant; inflorescences persistent.

*Inflorescence bud*.—Height: About 1.4 cm. Diameter: About 8 mm. Shape: Ovoid. Color: Close to 147B.

*Inflorescence size*.—Diameter: About 11 cm. Depth (height): About 3.5 cm. Disc diameter: About 3.3 cm. Receptacle height: About 2 cm. Receptacle diameter: About 1 cm. Receptacle shape: Conical, narrow. Receptacle color: Close to NN155B.

*Ray florets*.—Length: About 5.4 cm. Width: About 9 mm. Shape: Lanceolate. Apex: Acute to slightly praemorse. Base: Attenuate; fused into a short corolla tube. Texture, upper and lower surfaces: Smooth, glabrous; satiny. Number of ray florets per inflorescence: About 20 arranged in a single whorl. Aspect: Initially upright to outwardly arching; slightly concave along the longitudinal axis. Color: When opening, upper surface: Close to 34A. When opening, lower surface: Close to 36D faintly underlain with close to 46A. Fully opened, upper surface: Darker than 32A; with development, color becoming closer to 31C to 31D. Fully opened, lower surface: Close to 36D faintly underlain with close to 46A.

*Disc florets*.—Shape: Tubular; apex five-pointed. Length: About 1 cm. Diameter: About 1.5 mm. Number of disc florets per inflorescence: About 147. Texture: Smooth, glabrous. Color, immature and mature: Apex: Close to 144A. Mid-section and base: Close to NN155D.

*Receptacle spines*.—Quantity: One per disc floret. Length: About 1.5 cm. Width: About 1 mm. Shape: Acicular. Apex: Sharply acute. Base: Tapering. Texture: Smooth, glabrous. Color: Apex: Close to 17A and 21A and tinted with close to 53A. Mid-section: Close to 144A. Base: Close to NN155D.

*Phyllaries*.—Quantity per inflorescence: About 60 in about three to four whorls. Length, outer phyllaries: About 1.5 cm. Width, outer phyllaries: About 3 mm. Shape: Lanceolate. Apex: Acute. Base: Truncate. Margin: Entire. Texture, upper and lower surfaces: Smooth, glabrous. Color, upper and lower surfaces: Close to 147A.

*Peduncles*.—Length, terminal peduncle: About 7.5 cm. Length, uppermost axillary peduncle: About 4 cm. Diameter: About 3 mm. Angle, terminal peduncles: Erect. Angle, axillary peduncles: About 20° from vertical. Strength: Strong. Texture: Smooth, glabrous. Color: Close to 146B and 144A.

*Reproductive organs*.—Androecium: Stamens per disc floret: One. Filament length: About 1 cm. Filament color: Close to 145D. Anther shape: Oblong. Anther length: Less than 1 mm. Anther color: Close to 146C. Pollen amount: Scarce. Pollen color: Close to 21A. Gynoecium: Pistil length: About 1.2 cm. Stigma shape: Bi-parted; reflexed. Stigma color: Close to 187A. Style length: About 1 cm. Style color: Close to 150D. Ovary color: Close to 157A. Seeds/fruits: Seed and fruit development have not been observed on plants of the new *Echinacea*.

Disease/pest resistance: Plants of the new *Echinacea* have not been shown to be resistant to pathogens and pests common to *Echinacea*.

Garden performance: Plants of the new *Echinacea* have been observed to have good garden performance and to tolerate rain, wind and temperatures ranging from about −16° C. to about 37° C.

It is claimed:

1. A new and distinct *Echinacea* plant named 'Jacob Lewis' as illustrated and described.

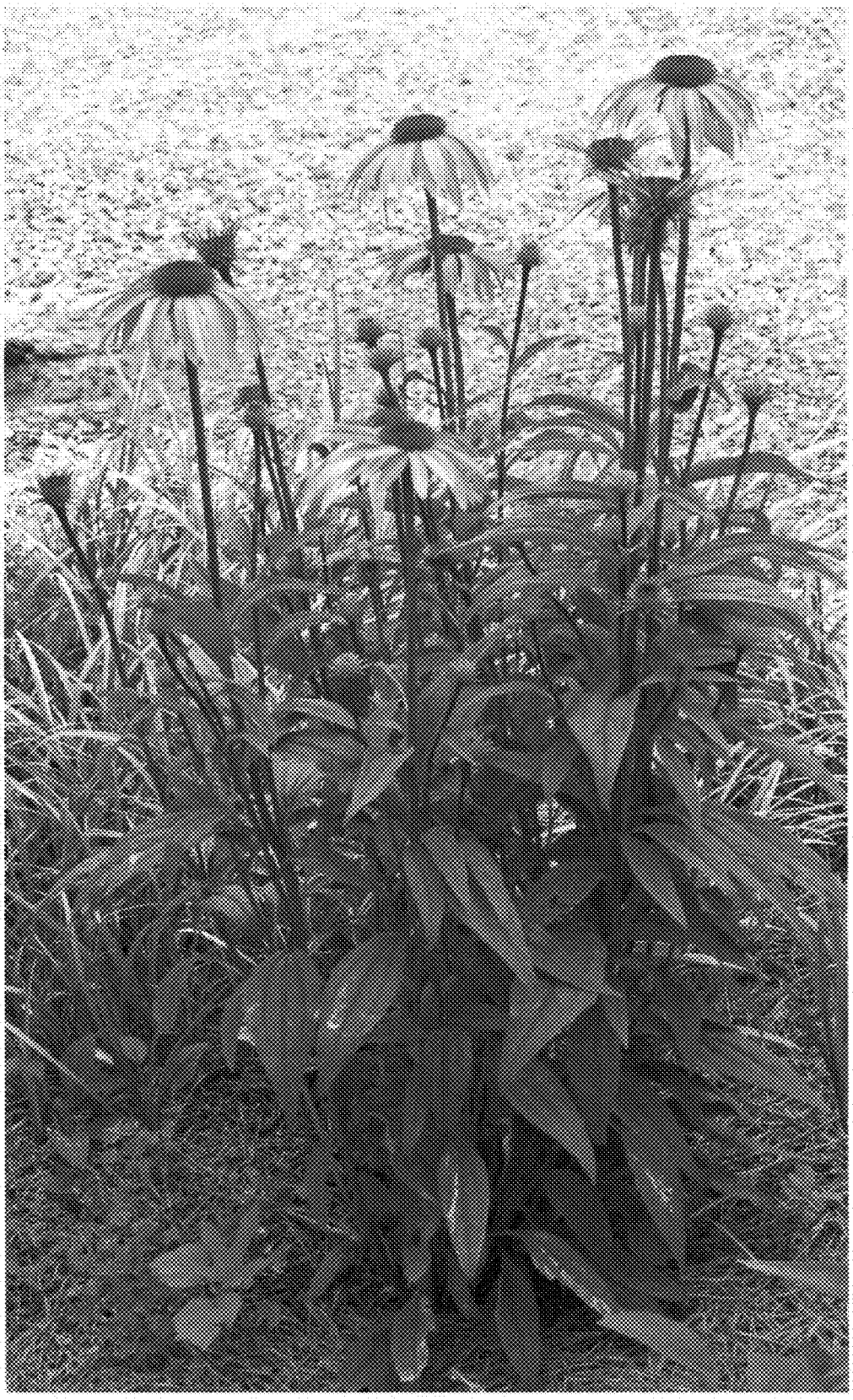

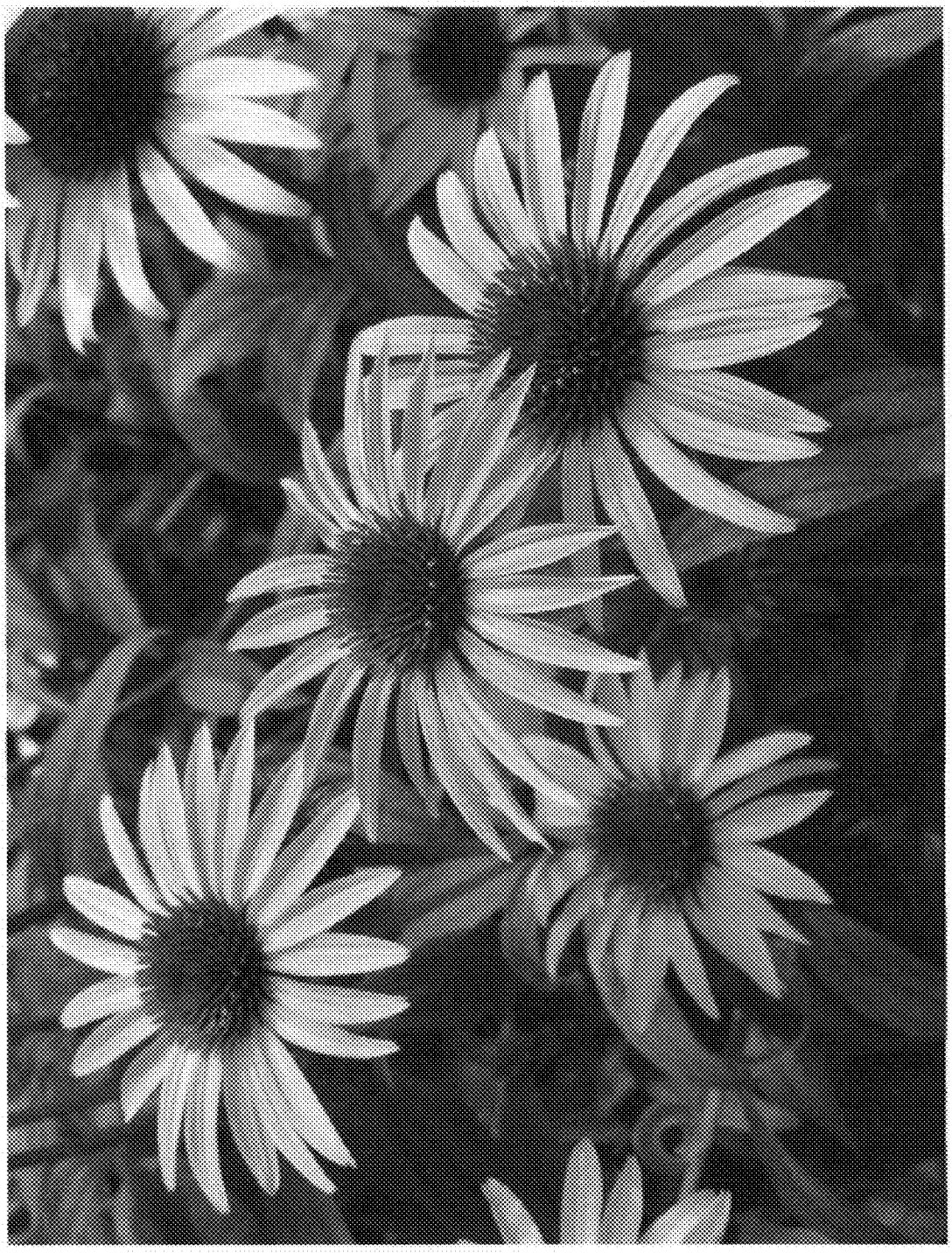

* * * * *